(12) United States Patent
Harttig

(10) Patent No.: US 8,496,876 B2
(45) Date of Patent: Jul. 30, 2013

(54) FOLDED CARRIER TAPE HAVING CONSUMABLE ELEMENTS

(75) Inventor: Herbert Harttig, Neustadt (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/183,825

(22) Filed: Jul. 15, 2011

(65) Prior Publication Data

US 2012/0009102 A1    Jan. 12, 2012

Related U.S. Application Data

(63) Continuation of application No. PCT/EP2009/009241, filed on Dec. 23, 2009.

(30) Foreign Application Priority Data

Jan. 15, 2009  (EP) .................................... 09000497

(51) Int. Cl.
*G01N 21/00*  (2006.01)

(52) U.S. Cl.
USPC ........................................................... 422/66

(58) Field of Classification Search
USPC ........................................................... 422/66
See application file for complete search history.

(56) References Cited

U.S. PATENT DOCUMENTS

| | | | |
|---|---|---|---|
| 2,989,212 | A | 6/1961 | Ekenstam et al. |
| 3,921,802 | A | 11/1975 | Thompson |
| 4,328,184 | A | 5/1982 | Kondo |
| 5,609,823 | A | 3/1997 | Harttig et al. |
| 2006/0173380 | A1 | 8/2006 | Hoenes et al. |
| 2007/0038150 | A1 | 2/2007 | Calasso et al. |
| 2008/0103415 | A1 | 5/2008 | Roe et al. |
| 2008/0286149 | A1* | 11/2008 | Roe et al. .......................... 422/58 |

FOREIGN PATENT DOCUMENTS

| | | |
|---|---|---|
| WO | 03045557 A2 | 6/2003 |
| WO | 2007077212 A2 | 7/2007 |
| WO | 2007147494 A2 | 12/2007 |

* cited by examiner

*Primary Examiner* — Lore Jarrett

(74) *Attorney, Agent, or Firm* — Harness, Dickey

(57) ABSTRACT

The invention relates to a carrier tape which carries a plurality of consumable elements for a system for determining an analyte concentration of a human or animal bodily fluid and is folded into a stack. According to the invention, the consumable elements are disposed on the carrier tape in groups, wherein the distance between adjacent groups in the longitudinal direction of the carrier tape is greater than that between adjacent consumable elements within a group.

19 Claims, 2 Drawing Sheets

FOLDED CARRIER TAPE HAVING CONSUMABLE ELEMENTS

CROSS-REFERENCE TO RELATED APPLICATIONS

This application is a continuation of International Patent Application No. PCT/EP2009/009241, filed Dec. 23, 2009, which claims the benefit and priority of European Patent Application No. 09000497.9, filed Jan. 15, 2009. The entire disclosures of the above applications are incorporated herein by reference.

BACKGROUND

The invention is directed to a carrier tape having consumable elements for determining an analyte concentration in human or animal body fluids.

Carrier tapes are described in U.S. 2008/0103415 A1, Roe et al., published May 1, 2008, which carry lancets as consumable elements and, folded into a stack, are disposed in a chamber of a magazine. Said magazine, in combination with a lancing device into which the magazine can be inserted, forms a system for determining an analyte concentration of a human or animal bodily fluid. Such systems and similar systems are used by diabetics, for example, who must check their blood glucose level several times a day and, for this purpose, require a sample of bodily fluid, typically blood and/or interstitial fluid, which is obtained from a small puncture wound.

In contrast to lancing systems having drum magazines, which typically contain only six or eight lancing elements, a carrier tape can provide a substantially greater supply of lancing elements. Systems comprising carrier tapes which carry a plurality of consumable elements therefore have the advantage that a user does not have to replace a carrier tape as often or, if disposable devices are used, obtain a new device as often.

Carrier tapes can be reeled onto a core of a spool in a magazine, as is described in U.S. 2006/0173380 A1, Hoenes et al., published Aug. 3, 2006, for instance. Such a core requires considerable installation space, however, in particular when relatively wide consumable elements are involved, which are damaged by a reeling radius that is too narrow. In contrast, magazines comprising carrier tapes folded into a stack enable better utilization of the available installation space.

SUMMARY

The problem addressed by the present invention is that of demonstrating a way to improve the storage of consumable elements in a compact space using a carrier tape of the initially stated type, which carries a plurality of consumable elements for a system for determining an analyte concentration and is folded into a stack. This problem is solved by a carrier tape having features described herein.

While the adjacent consumable elements in the case of the carrier tape described in U.S. 2008/0103415 A1 are all separated by the same distance, the consumable elements of a carrier tape according to the invention are disposed in groups. The distance between adjacent groups in the longitudinal direction of the carrier tape is greater than that between adjacent consumable elements within a group. The distance between adjacent groups is understood to mean the distance between the last consumable element of a group and the first consumable element of a subsequent group. In this case, the word "adjacent" refers to the arrangement on a carrier tape before folding.

The arrangement of the consumable elements according to the invention has the advantage that, even if the carrier tape is folded into a stack by regular zigzag folding, all of the consumable elements do not lie on top of one another. Instead, the consumable elements in the carrier tape stack according to the invention can form two or more consumable element stacks disposed next to one another. In this manner a more favorable ratio of the height of the carrier tape stack to the length or width thereof can be obtained, thereby improving the handling of a carrier tape stack according to the invention and enabling a greater supply of consumable elements to be stored in an ergonomic device.

The consumable elements of a carrier tape according to the invention can be lancing elements or test elements comprising detection reagents, such as test fields comprising detection reagents for photometric concentration determination. A carrier tape according to the invention can carry identical consumable elements, for example, consumable elements of only one type, such as only lancing elements or only test fields, or it can carry lancing elements as well as separate test elements. If the carrier tape carries different consumable elements, then each of the individual groups preferably contains a plurality of lancing elements and a plurality of test elements. It is preferable in particular for the consumable elements to be designed as lancing elements comprising integrated test elements, e.g. lancets having a capillary channel for drawing up bodily fluid, which leads to a test field with detection reagents.

In the case of a carrier tape according to the invention, the distance between adjacent consumable elements is preferably greater than the length of the stack as measured in the longitudinal direction of the carrier tape. It is thereby ensured that one layer of the carrier tape stack contains one consumable element at most. Although consumable elements can also be arranged in closer intervals on the carrier tape, so that one layer of the stack contains two, three, or even more consumable elements located next to one another, for instance, the individual consumable elements must then be positioned substantially more precisely on the tape during production. In contrast, greater distances between the individual consumable elements allow manufacturing tolerances to be greater, thereby reducing manufacturing costs. Particularly preferably, the distance between adjacent consumable elements is more than twice as great as the length of the stack as measured in the longitudinal direction of the carrier tape. It is thereby possible to orient the consumable elements in the carrier tape stack in a uniform manner with respect to the stacking direction, i.e. they always rest on the carrier tape section that carries them, in the stacking direction, for instance, or each of the consumable elements is located underneath the carrier tape section that carries it. It is advantageous in particular for the distance between adjacent consumable elements to be greater than the extension of one of the consumable elements in the longitudinal direction of the carrier tape plus twice the length of the stack as measured in the longitudinal direction of the carrier tape. It is thereby possible to dispose sequential consumable elements in the carrier band stack next to one another. The affixation of the consumable elements on one side of the carrier tape is particularly advantageous for manufacture and use.

It is particularly preferable for at least two carrier tape layers to always be disposed between two consumable elements which are located one above the other in a consumable element stack.

According to an advantageous refinement of the invention, the distances between one consumable element and the next identical consumable element are all the same within the groups. For example, three lancing elements can be arranged in one group, wherein the distance between the first and the second lancing element is equal to the distance between the second and the third lancing element. Test elements, for instance, as further consumable elements, can be arranged between the lancing elements, in order to examine samples of bodily fluid obtained from puncture wounds. The test elements can be disposed asymmetrically with respect to the lancing elements, and so each test element may be disposed closer to the lancing element which is used to obtain a sample to be examined using the test element. The distances between adjacent consumable elements are all preferably the same within the groups, however. Distances that are the same are understood to be distances that are the same within the scope of the manufacturing tolerances, i.e. they deviate from one another only by manufacturing tolerances.

According to another advantageous refinement of the invention, the distance between adjacent groups in each case is greater than twice, preferably greater than three times, the length of the stack as measured in the longitudinal direction of the carrier tape. It is thereby ensured that carrier tape loops that do not carry consumable elements can be laid down in the carrier tape stack. Such sections can be used to simplify the guidance and transport of the tape in a handheld device. For example, it is thereby possible for the carrier tape to comprise leading sections and trailing sections without consumable elements, which make it possible to easily utilize the first and the last consumable element of a carrier tape stack. The distance between adjacent groups is preferably always the same. In principle, however, the distance between adjacent groups can vary, in a regular manner in particular.

According to another advantageous refinement of the invention, each of the individual layers of the carrier tape stack has the same length. A carrier tape which has been folded into a stack in this manner is also referred to as a "leporello". A "leporello" is a strip that has been folded in the manner of an accordion. The fold edges of a "leporello" extend parallel to one another and perpendicularly to the longitudinal direction of the strip. It is also possible, however, to provide layers in the carrier tape stack that have different lengths, i.e. to fold the carrier tape with different distances.

Preferably, each of the groups of a carrier tape according to the invention comprises 2 to 8 consumable elements, particularly preferably 3 to 5 consumable elements. It is furthermore preferable for the carrier tape to carry at least 5 groups, in particular at least 10 groups. It is furthermore preferable for all groups between the first and the last group of a carrier tape to be identical, i.e. to contain the same number of consumable elements. The first and the last group can deviate in particular, e.g. can contain fewer consumable elements. Preferably, however, all groups are identical.

If the carrier tape carries different consumable elements, the various consumable elements preferably have the same thickness if an even number of consumable element stacks is present. For instance, if the number of consumable element stacks is even and two different consumable elements, e.g. lancing elements and test elements, are present, then the same consumable elements always lie on top of one another in a consumable element stack. In such a case it is favorable for the consumable elements to have the same thickness.

A carrier tape stack according to the invention can be disposed in a chamber of a magazine which, according to the intended use thereof, is inserted into a handheld device. Such a magazine preferably has a transport device, e.g. a reeling device, in order to draw the carrier tape out of the magazine chamber by reeling.

DRAWINGS

Further details and advantages of the invention are explained using embodiments, with reference to the attached drawings. Parts that are identical or similar are labeled using the same reference numerals. In the drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
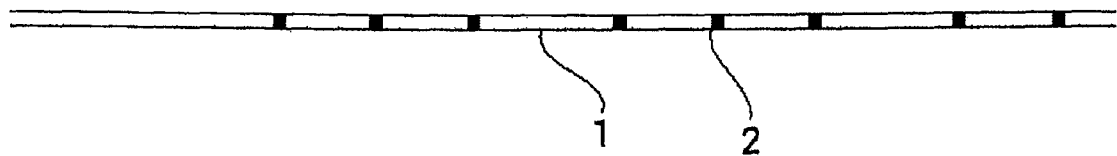
FIG. 1 shows a schematic depiction of a carrier tape having consumable elements.

Carrier tape 1 depicted in FIG. 1 carries consumable elements 2, such as lancing elements, which are disposed in a regular manner. Consumable elements 2 are disposed on carrier tape 1 in groups. In the embodiment shown, each said group comprises three consumable elements 2. The distance between adjacent groups is greater than that between adjacent consumable elements 2 within a group. In the embodiment shown, the distances between adjacent consumable elements 2 within the groups are all the same. Likewise, the distances between the individual groups are all the same, within the manufacturing tolerances.

Figure 2:
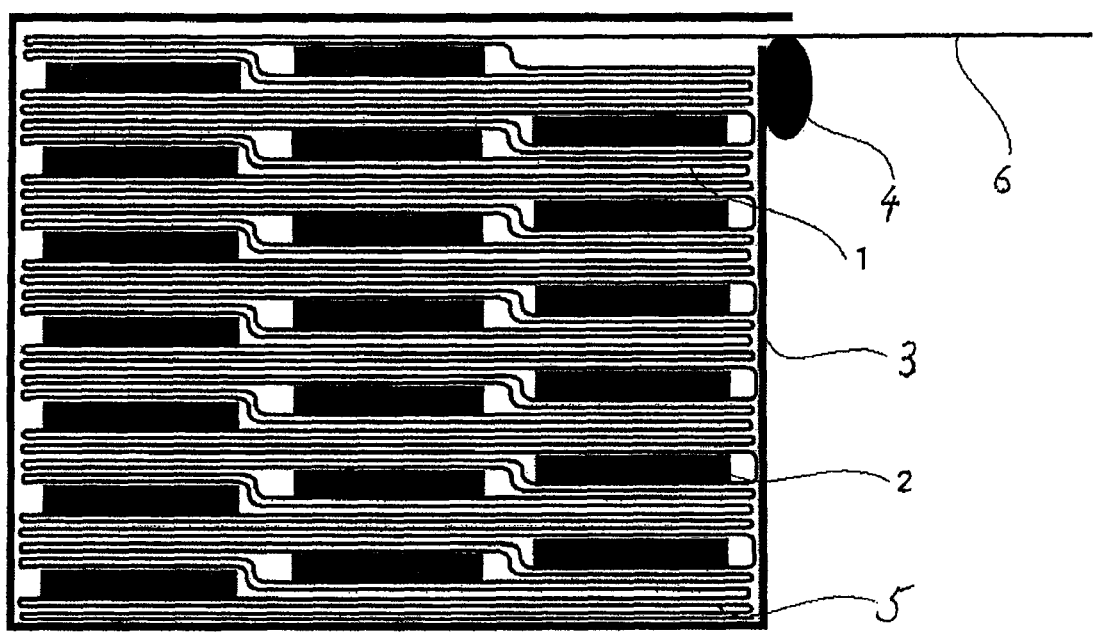
FIG. 2 shows a schematic depiction of a magazine chamber having a carrier tape stack disposed therein.

Carrier tape 1 is folded in a zigzag shape into a stack, i.e. into a "leporello", and is inserted into chamber 3 of a magazine. FIG. 2 shows a schematic depiction of an embodiment of a magazine chamber 3 in which a carrier tape 1 folded into a "leporello" stack is disposed. For clarity, the layers of carrier tape 1 are shown separated by an exaggerated distance in FIG. 2. Each layer contains one consumable element 2 at most, and all layers have the same length.

As shown in FIG. 2, consumable elements 2 in the carrier tape stack form consumable element stacks disposed next to one another. In a regular zigzag fold, the number of consumable element stacks is the same as the number of consumable elements 2 in the individual groups. In the embodiment shown, the stack of carrier tape 1 therefore contains three consumable element stacks. Adjacent consumable elements 2 are always disposed in different consumable element stacks.

In the stack of carrier tape 1, all consumable elements 2 are disposed in a uniform orientation. Therefore, in the embodiment shown, each consumable element 2 rests on the carrier tape section that carries it, in the stacking direction. This is achieved in that the distance between consumable elements 2 within one group in each case is more than twice as great as the length of the stack as measured in the longitudinal direction of carrier tape 1. In the embodiment shown, the distance between consumable elements 2 within one group in each case is slightly greater than the sum of twice the length of the carrier tape stack and the length of one consumable element 2 as measured in the longitudinal direction of carrier tape 1.

In the embodiment shown, the carrier tape stack between the last consumable element 2 of one group and the first consumable element 2 of a subsequent group contains a carrier tape loop that does not carry a consumable element 2. This is achieved in that the distance between adjacent groups in each case is greater than three times the length of the carrier tape stack. In the embodiment shown, the distance between adjacent groups is slightly greater than four times the length of the carrier tape stack.

Magazine chamber 3 comprises an opening through which carrier tape 1 is fed. A pull-through seal 4 is disposed at the opening of magazine chamber 3 to restrain dirt or moisture from entering magazine chamber 3. Pull-through seal 4 can be designed e.g. as a lip composed of an elastomeric material. For clarity, carrier tape 1 and the edge of the opening of magazine chamber 3 further away from pull-through seal 4 are shown separated by a distance in FIG. 2. Preferably, however, carrier tape 1 is pressed against the edge of the opening by pull-through seal 4. In particular, pull-through seal 4 preferably acts on the side of carrier tape 1 on which no consumable elements 2 are disposed.

The carrier tape stack inserted into magazine chamber 3 has a tape trailing section 5 on the end thereof, and a tape leading section 6 at the beginning thereof. It is thereby ensured that the first and the last consumable element 2 of carrier tape 1 can also be easily used.

Figure 3:
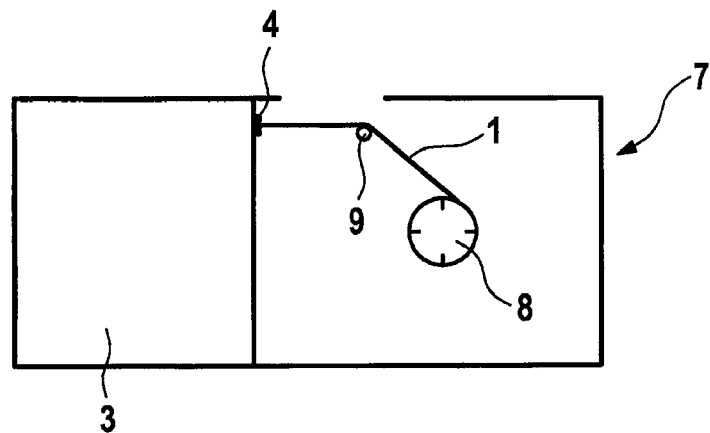
FIG. 3 shows a schematic depiction of a magazine.

FIG. 3 is a schematic illustration of a complete magazine 7 comprising a magazine chamber 3, which contains a carrier tape stack, and a reeling device 8 for reeling carrier tape 1. Carrier tape 1 is routed out of magazine chamber 3, past pull-through seal 4, over redirection device 9 to reeling device 8, onto which tape leading section 6 of carrier tape 1 is fastened. By rotating reeling device 8, carrier tape 1 can be pulled out of magazine chamber 3, thereby enabling consumable elements 2 to be used one after the other.

Figures 4A, 4B:
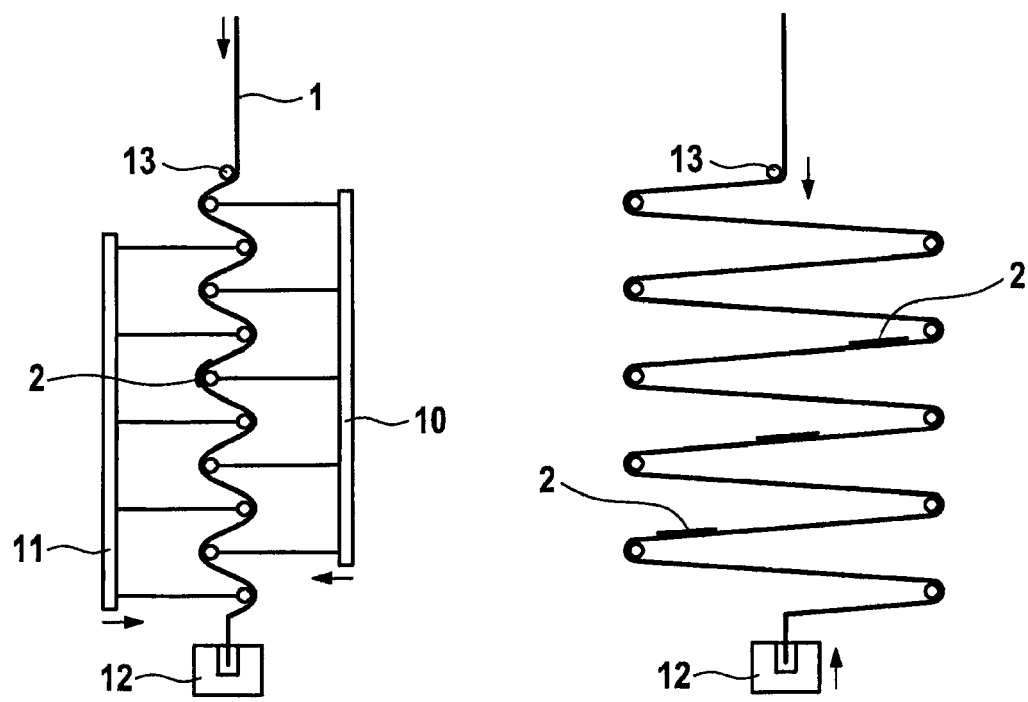
FIGS. 4a and 4b show schematic depictions to illustrate a method for folding a carrier tape.

FIGS. 4a and 4b schematically illustrate how a carrier tape 1 can be folded into a stack. For folding, carrier tape 1 is guided over rollers of two roller frames 10, 11. The rollers, which are arranged in the manner of a comb, are slid past one another with the frame. The carrier tape therefore follows a zigzag course. In the maximum distance of the rollers, carrier tape 1 is pressed together into a stack by a gripper 12 and a redirection device 13. The rollers are then pulled out of the tape loops perpendicularly to the tape direction. After the tape feed section is cut off, the folded stack can be placed in a magazine chamber 3.

The rollers shown can be replaced by deflection pins. Furthermore, the rollers do not necessarily have to be moved simultaneously, but rather can be moved from the bottom to the top in alternation. Instead of roller frame 10, 11, it is also possible to use a type of large, interlocking toothed wheels.

Carrier tape 1 is preferably a film made of plastic, such as polyester. Other materials, such as paper or metal foil, can also be used, however.

REFERENCE NUMERALS

1 Carrier tape
2 Consumable element
3 Magazine chamber
4 Pull-through seal
5 Tape trailing section
6 Tape leading section
7 Magazine
8 Reeling device
9 Redirection device
10 Roller frame
11 Roller frame
12 Gripper
13 Redirection device

What is claimed is:

1. A carrier tape for a system for determining an analyte concentration of a human or animal bodily fluid, comprising: a plurality of consumable elements that are disposed on the carrier tape in groups, wherein a first distance between adjacent groups in the longitudinal direction of the carrier tape is greater than a second distance between adjacent consumable elements within a group, wherein the carrier tape is folded into a plurality of layers forming a stack configured for placement within a magazine chamber.

2. The carrier tape according to claim 1, characterized in that at least a few of the consumable elements are lancing elements and/or test elements, or lancing elements with integrated test elements.

3. The carrier tape according to claim 1, characterized in that each group contains at least three consumable elements.

4. The carrier tape according to claim 1, characterized in that the second distance is greater than a length of the magazine chamber as measured in the longitudinal direction of the carrier tape.

5. The carrier tape according to claim 1, characterized in that the second distance is greater than the extension of one of the consumable elements in the longitudinal direction of the carrier tape plus twice a length of the magazine chamber as measured in the longitudinal direction of the carrier tape.

6. The carrier tape according to claim 1, characterized in that each layer of the plurality of layers contains one consumable element at most.

7. The carrier tape according to claim 1, characterized in that the first distance is greater than twice a length of the magazine chamber as measured in the longitudinal direction of the carrier tape.

8. The carrier tape according to claim 7, characterized in that the distance between adjacent groups in each case is greater than three times a length of the magazine chamber as measured in the longitudinal direction of the carrier tape.

9. The carrier tape according to claim 1, characterized in that the distances between one consumable element and the next identical consumable element are all the same within the groups.

10. The carrier tape according to claim 1, characterized in that the distances between adjacent consumable elements are all the same within the groups.

11. The carrier tape according to claim 1, characterized in that the distances between adjacent groups are all the same.

12. The carrier tape according to claim 1, characterized in that the plurality of layers are arranged such that the consumable elements in the stack form at least two consumable element columns disposed next to one another.

13. The carrier tape according to claim 12, characterized in that adjacent consumable elements are always disposed in different consumable element columns.

14. The carrier tape according to claim 1, characterized in that each layer of the plurality of layers has the same length.

15. A magazine for a system for determining an analyte concentration of a human or animal bodily fluid, the magazine comprising:
a chamber;
a carrier tape folded into a plurality of layers and forming a stack disposed in the chamber; and
a plurality of consumable elements disposed on the carrier tape in groups, wherein a first distance between adjacent groups in the longitudinal direction of the carrier tape is greater than a second distance between adjacent consumable elements within a group.

16. The magazine according to claim 15, further comprising a reeling device for reeling the carrier tape.

17. A carrier tape comprising: a plurality of consumable elements for a system for determining an analyte concentration of a human or animal bodily fluid, wherein the carrier tape is folded in a zigzag shape into a stack having a plurality of layers such that the consumable elements are disposed on the layers of the carrier tape stack to form at least three consumable element columns disposed next to one another.

18. The carrier tape according to claim 17, wherein the plurality of consumable elements are disposed on the carrier tape in groups, further wherein a first distance between adjacent groups in the longitudinal direction of the carrier tape is greater than a second distance between adjacent consumable elements within a group.

19. The carrier tape according to claim 17, wherein each layer of the plurality of layers has the same length.

* * * * *